United States Patent
Yoshikawa et al.

(10) Patent No.: US 9,464,018 B2
(45) Date of Patent: Oct. 11, 2016

(54) METHOD FOR PRODUCING DIALDEHYDE

(71) Applicant: KURARAY CO., LTD., Kurashiki-shi (JP)

(72) Inventors: Tatsuya Yoshikawa, Kamisu (JP); Tomoaki Tsuji, Kamisu (JP)

(73) Assignee: KURARAY CO., LTD., Kurashiki-shi (JP)

( * ) Notice: Subject to any disclaimer, the term of this patent is extended or adjusted under 35 U.S.C. 154(b) by 0 days.

(21) Appl. No.: 14/778,784

(22) PCT Filed: Mar. 17, 2014

(86) PCT No.: PCT/JP2014/057169
§ 371 (c)(1),
(2) Date: Sep. 21, 2015

(87) PCT Pub. No.: WO2014/156776
PCT Pub. Date: Oct. 2, 2014

(65) Prior Publication Data
US 2016/0052852 A1 Feb. 25, 2016

(30) Foreign Application Priority Data

Mar. 27, 2013 (JP) ................................. 2013-067516

(51) Int. Cl.
C07C 45/50 (2006.01)
B01J 31/22 (2006.01)
C07C 47/12 (2006.01)

(52) U.S. Cl.
CPC .............. *C07C 45/505* (2013.01); *B01J 31/22* (2013.01); *C07C 45/50* (2013.01); *C07C 47/12* (2013.01)

(58) Field of Classification Search
CPC ............................ C07C 45/50; C07C 45/505
USPC ....................................................... 568/454
See application file for complete search history.

(56) References Cited

U.S. PATENT DOCUMENTS

| | | | |
|---|---|---|---|
| 4,808,756 A | 2/1989 | Tokitoh et al. | |
| 6,100,432 A | 8/2000 | Borgel et al. | |
| 2003/0013919 A1 | 1/2003 | Walczuch et al. | |
| 2007/0004939 A1 | 1/2007 | Volland et al. | |
| 2009/0259073 A1 | 10/2009 | Sugioka et al. | |
| 2012/0108852 A1 | 5/2012 | Greb et al. | |

FOREIGN PATENT DOCUMENTS

| | | |
|---|---|---|
| CN | 1222904 A | 4/1997 |
| CN | 1871199 A | 11/2006 |
| JP | 62-270541 A | 11/1987 |
| JP | 11-511159 A | 9/1999 |
| JP | 2004-506602 A | 3/2004 |
| JP | 2007-509093 A | 4/2007 |
| JP | 2008-31125 A | 2/2008 |
| JP | 2012-522813 A | 9/2012 |
| WO | 2007/114445 A1 | 10/2007 |

OTHER PUBLICATIONS

Charles P. Casey, et al., "Diphosphines with Natural Bite Angles near 120° Increase Selectivity for n-Aldehyde Formation in Rhodium-Catalyzed Hydroformylation," J. Am. Chem. Soc., vol. 114, No. 14, 1992, pp. 5535-5543.
Bahram Moasser, et al., "Mechanistic Aspects of a Highly Regioselective Catalytic Alkene Hydroformylation using a Rhodium Chelating Bis(phosphite) Complex," Organometallics, vol. 14, No. 8, 1995, pp. 3832-3838.
International Search Report issued Apr. 28, 2014 in PCT/JP2014/057169 filed Mar. 17, 2014.
Written Opinion issued May 3, 2016 in Singaporean Patent Application No. 11201507901W.
Chinese Office Action issued on Jun. 3, 2016 in corresponding Chinese Patent Application No: 201480017693.3, 7 pp.

*Primary Examiner* — Sikarl Witherspoon
(74) *Attorney, Agent, or Firm* — Oblon, McClelland, Maier & Neustadt, L.L.P.

(57) ABSTRACT

Provided is an industrially advantageous method for producing a dialdehyde having a production ratio of linear dialdehydes to branched dialdehydes of 80/20 to 90/10, with an amount of rhodium to be used that is lower than that in the related art. Specifically, provided is a method for producing a dialdehyde, including reacting a linear olefinic compound having each of an ethylenic double bond and an aldehyde group on each end of the molecule with carbon monoxide and hydrogen, in the presence of a rhodium catalyst comprised of a bisphosphite represented by General Formula (I) and a rhodium compound, in which the reaction pressure of a mixed gas formed of carbon monoxide and hydrogen is decreased as the reaction proceeds, wherein R represents a hydrogen atom, an alkyl group having 1 to 4 carbon atoms, or an alkoxy group having 1 to 4 carbon atoms, and W represents an alkylene group having 1 to 20 carbon atoms, a cycloalkylene group having 5 to 18 carbon atoms, or an alkylene-arylene group having 7 to 11 carbon atoms, and a rhodium compound.

7 Claims, No Drawings

METHOD FOR PRODUCING DIALDEHYDE

TECHNICAL FIELD

The present invention relates to a method for producing a dialdehyde. Specifically, the present invention relates to an industrially advantageous method for producing a dialdehyde having a linear dialdehyde content of 80% by mass to 90% by mass by hydroformylation of a linear olefinic compound having each of an ethylenic double bond and an aldehyde group on each end of the molecule. The method of the present invention is useful as, for example, a method for producing a dialdehyde mixture of 1,9-nonanedial/2-methyl-1,8-octanedial which is a synthesis intermediate of a diol mixture of 1,9-nonanediol and 2-methyl-1,8-octanediol (a content of 1,9-nonanediol of 80% by mass to 90% by mass) from 7-octen-1-al. The diol mixture of 1,9-nonanediol and 2-methyl-1,8-octanediol is commercially available under a trade name of "ND15" from Kuraray Co., Ltd., and is useful as a raw material for producing polycarbonates, polyesters, polyurethanes, or the like, a raw material for paints (polyester paints or epoxy resin paint), a resin modifier for polyester resins or epoxy resins, or the like.

BACKGROUND ART

A reaction in which an olefinic compound having a carbon-carbon double bond is reacted with carbon monoxide and hydrogen in the presence of a rhodium catalyst comprised of a rhodium compound and a phosphorous compound to be converted into an aldehyde is referred to as a hydroformylation reaction, and a method for producing an aldehyde using this reaction is of a high industrial value.

A compound having an ethylenic double bond on an end of the molecule is subjected to a hydroformylation reaction to generate a linear aldehyde and a branched aldehyde. Further, in some cases, isomers formed by isomerization of double bonds and aldehydes formed by hydroformylation of the isomers are by-produced.

The catalytic activity, the linear aldehyde selectivity, and the production ratio of linear aldehydes to branched aldehydes in the hydroformylation reaction vary depending on all the reaction conditions for hydroformylation, such as a reaction temperature, the compositional ratio of a mixed gas including carbon monoxide and hydrogen, the pressure of the mixed gas, the type and the use amount of a solvent, the structure of a terminal olefin compound, and the type of a phosphorous compound constituting a rhodium catalyst, for example. In particular, from the viewpoints that the type of the phosphorous compound constituting a rhodium catalyst significantly changes the electronic state of a rhodium atom, which is a central atom in the rhodium catalyst, and the steric structure in the periphery of a central rhodium metal in a rhodium complex intermediate which is a genuine active species of the rhodium catalyst, it has been known that the effects on a catalytic activity, a linear aldehyde selectivity, and a production ratio of linear aldehydes to branched aldehydes are significant (see NPLs 1 and 2).

Rhodium is expensive, and thus, in order to carry out a hydroformylation reaction in an industrially advantageous manner, it is important to achieve a decrease in the amount of rhodium to be used due to an improved catalytic activity; improve an aldehyde selectivity; and control the production ratio of linear aldehydes to branched aldehydes to a desired range at the same time so as to reduce the production cost in a plant for aldehydes. Further, various bisphosphites have been developed and have been reported in order to achieve such purposes.

On the other hand, a method for producing a linear dialdehyde by subjecting a linear olefinic compound each having an ethylenic double bond on an end of the molecule and an aldehyde group (hereinafter referred to as a linear unsaturated aldehyde in some cases) to hydroformylation has been known.

For example, the production ratios of linear dialdehydes (1,9-nonanedial; hereinafter referred to as NL) to branched dialdehydes (2-methyl-1,8-octanedial; hereinafter referred to as MOL) and the dialdehyde selectivity in a hydroformylation reaction of 7-octen-1-al using a bisphosphite having a specific structure, typically bisphosphite A, bisphosphite B, bisphosphite C, or the like as shown below, have been disclosed (see PTL 1).

Specifically, it is shown that in a case of using the bisphosphite A, an dialdehyde with NL/MOL=85.1/14.9 was obtained with a selectivity of 97.0%; in a case of using the bisphosphite B under the same conditions, an dialdehyde with NL/MOL=79.8/21.2 was obtained with a selectivity of 97.0%; and in a case of using the bisphosphite C under the same conditions, an dialdehyde with NL/MOL=79.7/20.3 was obtained with a selectivity of 97.7%.

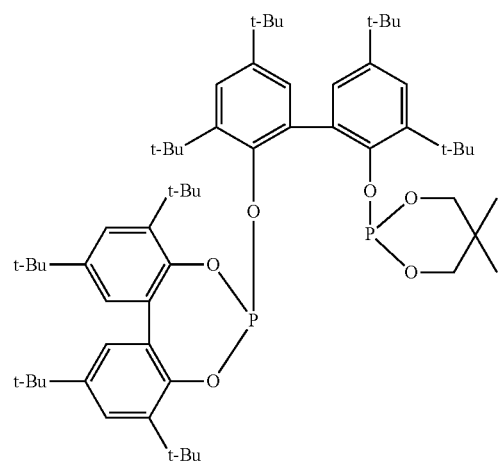

Bisphosphite A

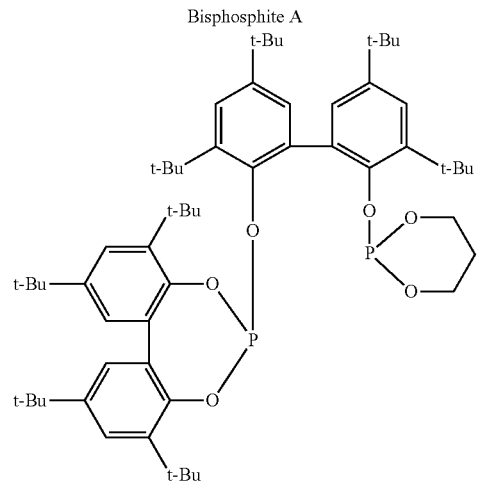

Bisphosphite B

-continued

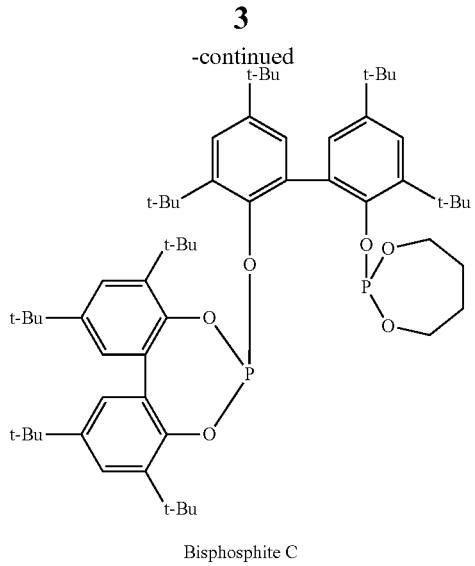

Bisphosphite C

Furthermore, in PTL 1, the stability of bisphosphite is disclosed. Specifically, it is shown that in a case of adding 100 mg (0.102 mmol) of bisphosphite A to 100 ml of toluene containing 70 ppm of water (0.337 mmol as water) (condition under which water is present at 3.3 molar times with respect to bisphosphite A), followed by carrying out a treatment at 125° C. under a nitrogen atmosphere, the residual rate of the bisphosphite A after 3 hours is 70%.

CITATION LIST

Patent Literature

[PTL 1] JP-A-2008-31125

Non Patent Literature

[NPL 1] Journal of American Chemical Society, vol. 114, 1992, pp. 5535 to 5543
[NPL 2] Organometallics, vol. 14, 1995, pp. 3832 to 3838

SUMMARY OF INVENTION

Technical Problem

In Examples of PTL 1, the amount of rhodium to be used with respect to 1 kg of 7-octen-1-al is 0.025 mmol in terms of rhodium atoms, and from the viewpoint of cutting down the cost of a catalyst in the production cost for a dialdehyde, there are still needs for improvement.

On the other hand, from an industrial point of view, there are some cases where water and/or a carboxylic acid is/are contained in a linear unsaturated aldehyde such as 7-octen-1-al, which is used as a raw material. In the related cases, it can be said that it is considered that sufficient reaction results cannot be obtained from the stability of bisphosphite A disclosed in PTL 1, and thus, there are still needs for improvement.

Solution to Problem

The present inventors have found that in a hydroformylation reaction of a linear unsaturated aldehyde, in particular 7-octen-1-al, it is unexpectedly possible to maintain a catalytic activity even with a smaller amount of rhodium than that in a conventionally disclosed method, and the selectivity for dialdehydes and the production ratios of linear dialdehydes and branched dialdehydes can be controlled by decreasing the reaction pressure of a mixed gas including carbon monoxide and hydrogen as the reaction proceeds, for example, by controlling the reaction pressure of a mixed gas formed of carbon monoxide and hydrogen to 30% to 80% of the pressure at a time of initiation of the reaction in a step with a conversion of more than 70%. Further, the present inventors have also found that even in a case where at a time of initiation of the reaction, the reaction solution contains water and/or a carboxylic acid to an amount in a constant range, the equivalent reaction results can be achieved, and have further conducted investigations, thereby completing the present invention.

That is, the present invention relates to the following:

[1] a method for producing a dialdehyde, including reacting a linear olefinic compound having each of an ethylenic double bond and an aldehyde group on each end of the molecule (linear unsaturated aldehyde) with carbon monoxide and hydrogen in the presence of a rhodium catalyst comprised of a bisphosphite (hereinafter referred to as a bisphosphite (I)) represented by General Formula (I) and a rhodium compound, in which the reaction pressure of a mixed gas formed of carbon monoxide and hydrogen is decreased as the reaction proceeds:

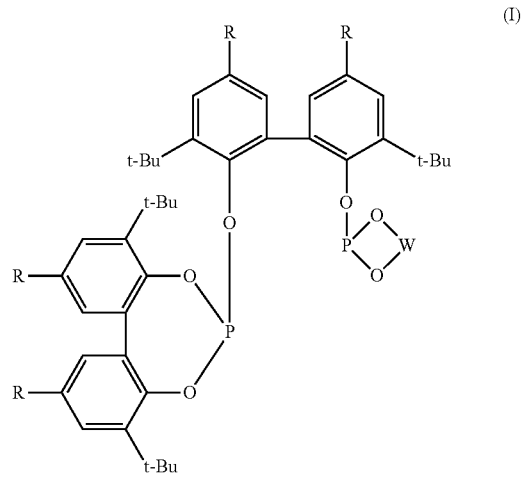

wherein R represents a hydrogen atom, an alkyl group having 1 to 4 carbon atoms, or an alkoxy group having 1 to 4 carbon atoms, W represents an alkylene group having 1 to 20 carbon atoms, a cycloalkylene group having 5 to 18 carbon atoms, or an alkylene-arylene group having 7 to 11 carbon atoms;

[2] the method for producing a dialdehyde as described in [1], in which the content of water in the reaction solution at a time of initiation of the reaction is 0.1 mmol/kg to 500 mmol/kg, and the content of a carboxylic acid in the reaction solution is 0.1 mmol/kg to 50 mmol/kg in terms of carboxyl groups;

[3] the method for producing a dialdehyde as described in [1] or [2], in which the reaction pressure of the mixed gas formed of carbon monoxide and hydrogen is controlled stepwise or continuously to 30% to 80% of the pressure at a time of initiation of the reaction in a step in which the conversion of the linear unsaturated aldehyde is more than 70%;

[4] the method for producing a dialdehyde as described in [3], in which a plurality of reactors are connected, the reaction is carried out in a first reactor until the conversion of the linear unsaturated aldehyde is more than 70%, and then the reaction solution in the first reactor is transferred to a second reactor in which the reaction pressure of the mixed gas formed of carbon monoxide and hydrogen is 30% to 80% of one of the first reactor to successively carry out the reaction;

[5] the method for producing a dialdehyde as described in any one of [1] to [4], in which the linear unsaturated aldehyde is any one of 5-hexen-1-al, 6-hepten-1-al, 7-octen-1-al, 8-nonen-1-al, 9-decen-1-al, 10-undecen-1-al, and 11-dodecen-1-al;

[6] the method for producing a dialdehyde as described in any one of [1] to [5], in which a bisphosphite (I) of General Formula (I), in which R is an alkyl group having 1 to 4 carbon atoms or an alkoxy group having 1 to 4 carbon atoms, and W is an alkylene group having 1 to 20 carbon atoms, is used;

[7] the method for producing a dialdehyde as described in [6], using a bisphosphite (I), in which R is a t-butyl group and W is an alkylene group having 2 to 5 carbon atoms; and

[8] the method for producing a dialdehyde as described in any one of [1] to [7], in which the concentration of rhodium in the reaction solution is $1.0 \times 10^{-4}$ mmol/kg to $6.0 \times 10^{-1}$ mmol/kg in terms of rhodium atoms, the amount of bisphosphite to be used is 1 molar times to 100 molar times in terms of rhodium atoms, the reaction temperature is 50° C. to 130° C., the compositional ratio of carbon monoxide to hydrogen is carbon monoxide/hydrogen=0.1/1 to 10/1 in terms of molar ratio, and the pressure at a time of initiation of the reaction is 0.5 MPa to 10 MPa (gauge pressure).

Advantageous Effects of Invention

According to the present invention, a dialdehyde having a production ratio of linear dialdehydes to branched dialdehydes of 80/20 to 90/10, with an amount of rhodium to be used, which is lower than that in the related art, can be produced in an industrially advantageous manner. The method of the present invention is useful as, for example, a method for producing a dialdehyde mixture (NL/MOL=80/20 to 90/10) with 1,9-nonanedial/2-methyl-1,8-octanedial (NL/MOL), which becomes a synthesis intermediate of a diol mixture of 1,9-nonanediol and 2-methyl-1,8-octanediol (a content of 1,9-nonanediol of 80% by mass to 90% by mass), from 7-octen-1-al.

DESCRIPTION OF EMBODIMENTS

Hereinbelow, the production method of the present invention will be described in detail.

In the production method of the present invention, a solution having a rhodium compound dissolved in a solvent and a solution having a bisphosphite (I) dissolved in a solvent may each be supplied to a hydroformylation reaction system to form a rhodium catalyst in the reaction system, or a rhodium compound and a bisphosphite (I) are dissolved in a solvent in an inert gas atmosphere, and then preferably stirred in an atmosphere of a mixed gas formed of carbon monoxide and hydrogen to prepare a solution of the rhodium catalyst separately, and such a solution of the rhodium catalyst may also be supplied to a hydroformylation reaction system. From the viewpoint of sufficiently expressing the catalytic activity, a method in which a solution of the rhodium catalyst is separately prepared and then supplied to a hydroformylation reaction system is preferred.

Examples of the rhodium compound for use in the production method of the present invention include $Rh(NO_3)_2$, $Rh(OAc)_2$, $Rh(acac)(CO)_2$, $Rh(acac)(CO)(PPh_3)$, $HRh(CO)(PPh_3)_3$, $RhCl(CO)(PPh_3)_2$, $RhBr(CO)(PPh_3)_2$, $RhCl(PPh_3)_3$, $[Rh(\mu\text{-}OAc)(CO)_2]_2$, $[Rh(\mu\text{-}OAc)(COD)]_2$, $[Rh(\mu\text{-}Cl)(COD)]_2$, $[Rh(\mu\text{-}Cl)(CO)b\ 2]_2$, $Rh_4(CO)_{12}$, $Rh_4(CO)_8(PPh_3)_4$, and $Rh(CO)_{16}$, (Further, OAc represents an acetyl group, acac represents an acetylacetonate group, Ph represents a phenyl group, and COD represents 1,5-cyclooctadiene). Among these, from the viewpoint that a rhodium catalyst can be easily prepared in an atmosphere of a mixed gas formed of carbon monoxide and hydrogen, it is preferable to use $Rh(acac)(CO)_2$.

In the production method of the present invention, the bisphosphite (I) represented by General Formula (I) may be used as a component constituting the rhodium catalyst for use in the production method of the present invention:

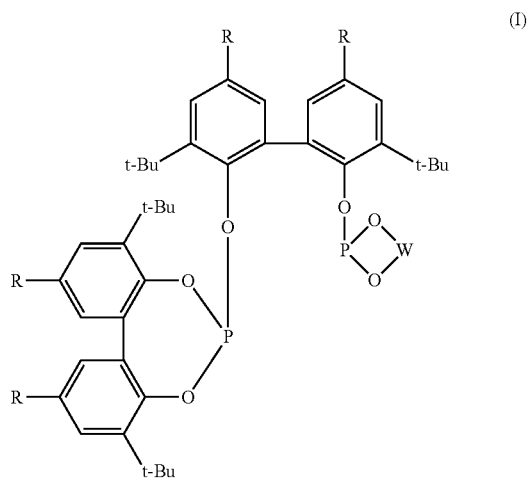

wherein R and W are as defined above.

Examples of the alkyl group having 1 to 4 carbon atoms, which is represented by R, include a methyl group, an ethyl group, an n-propyl group, an isopropyl group, an n-butyl group, a sec-butyl group, and a t-butyl group, and examples of the alkoxy group having 1 to 4 carbon atoms include a methoxy group, an ethoxy group, an n-propoxy group, an isopropoxy group, an n-butoxy group, a sec-butoxy group, and a t-butoxy group. Among these, the alkyl group having 1 to 4 carbon atoms is preferred, and the t-butyl group is still more preferred.

Examples of the alkylene group having 1 to 20 carbon atoms, which is represented by W, include a methylene group, a 1,2-ethylene group, a 1,2-dimethylethylene group, a 1,2-propylene group, a 2-methyl-1,2-propylene group, a 1,3-propylene group, a 1-methyl-1,3-propylene group, a 2-methyl-1,3-propylene group, a 1,2-dimethyl-1,3-propylene group, a 2,2-dimethyl-1,3-propylene group, a 1,4-butylene group, a 2,4-pentylene group, a hexamethylene group, an octamethylene group, a tetramethylethylene group, and a tetramethylene group; examples of the cycloalkylene group having 5 to 18 carbon atoms include a cyclopropylene group, a 1,2-cyclopentylene group, a 1,3-cyclopentylene group, a 1,2-cyclohexylene group, a 1,3-cyclohexylene group, and a 1,4-cyclohexylene group; and examples of the alkylene-arylene group having 7 to 11 carbon atoms include a benzylene group having an alkyl group (a methyl group, an ethyl group, an n-propyl group, an isopropyl group, an n-butyl group, a sec-butyl group, or a t-butyl group) as a substituent. Among these, the alkylene group having 2 to 5 carbon atoms is preferred, and the 1,2-ethylene group, the 1,2-dimethylethylene group, the 1,2-propylene group, the 2-methyl-1,2-propylene group, the 1,3-propylene group, the 1-methyl-1,3-propylene group, the 2-methyl-1,3-propylene group, the 1,2-dimethyl-1,3-propylene group, the 2,2-dimethyl-1,3-propylene group, and the 1,4-butylene group are still more preferred.

As a solvent for use in the preparation of a rhodium catalyst, an aprotic solvent is preferred from the viewpoint of inhibiting the hydrolysis of the bisphosphite (I); and the same type as a solvent inert to the reaction coexisting in the hydroformylation reaction, if necessary, is preferred from the viewpoint of recovering and using the solvent. Examples of the related solvent include saturated aliphatic hydrocarbons such as pentane, hexane, heptane, octane, nonane, decane, and cyclohexane; aromatic hydrocarbons such as benzene, toluene, ethylbenzene, propylbenzene, butylbenzene, o-xylene, m-xylene, p-xylene, o-ethyltoluene, m-ethyltoluene, and p-ethyltoluene; alcohols such as isopropanol, isobutanol, and neopentyl alcohol; ethers such as diethyl ether, dipropyl ether, butylmethyl ether, t-butylmethyl ether, dibutyl ether, ethylphenyl ether, diphenyl ether, tetrahydrofuran, and 1,4-dioxane; and ketones such as acetone, ethylmethyl ketone, methylpropyl ketone, diethyl ketone, ethylpropyl ketone, and dipropyl ketone. These solvents may be used singly or in combination of two or more kinds thereof. Among these, it is preferable to use toluene or tetrahydrofuran from the viewpoint that the rhodium compound and the bisphosphite (I) are uniformly dissolved with a small amount of solvent to be used.

It is preferable to increase the concentration of the rhodium atoms included in the solution of the rhodium catalyst as much as possible from the viewpoint of reduction in the amount of the solvent to be used, and it is preferable that the solution of the rhodium catalyst is prepared in a batch or semi-batch mode using a complete mixing bath type reactor from the viewpoint of strictly controlling the amount of bisphosphite to be used with respect to 1 mole of the rhodium atoms.

Specifically, a method in which a solution of the rhodium compound and a solution of the bisphosphite (I), separately prepared, are introduced to each of the reactors, a method in which any one of the solutions is placed in a reactor and the other is introduced as a solid, a method in which any one is placed in a reactor as a solid and the other is introduced as a solution, a method in which both are placed in a reactor as solids, and a method in which solvents is placed in a reactor and both are introduced as solids are given.

It is preferable to prepare a solution of the rhodium catalyst in an atmosphere of an inert gas such as nitrogen, argon, and helium, and it is also preferable to use nitrogen from the viewpoints of industrial availability and cost. The pressure of the inert gas is not particularly limited, but a range of normal pressure to 0.5 MPa (gauge pressure) is usually preferred.

In the preparation of a solution of the rhodium catalyst, the amount of the bisphosphite (I) to be used is preferably 1 molar times to 100 molar times, and more preferably 2 molar times to 20 molar times, with respect to the rhodium atoms. Within the above range, both of the catalytic activity and the dialdehyde selectivity are improved, and thus, the effects of the present invention are further improved.

The temperature at a time of preparing a rhodium catalyst for use in the production method of the present invention is preferably 10° C. to 80° C., and more preferably 20° C. to 50° C.

It is preferable that the solution of the rhodium catalyst prepared in an inert gas atmosphere in advance in an atmosphere of a mixed gas formed of carbon monoxide and hydrogen before being supplied to a hydroformylation reaction system. The pressure of the mixed gas formed of carbon monoxide and hydrogen is not particularly limited, but it is usually normal pressure to 0.5 MPa (gauge pressure).

The production method of the present invention can be carried out by introducing a rhodium catalyst preferably as a solution into a linear unsaturated aldehyde in the presence of a mixed gas formed of carbon monoxide and hydrogen.

The production method of the present invention can be carried out in a batch or semi-batch mode, using a complete mixing bath type reactor, and may be carried out in a flow and continuous mode, using a complete mixing bath type reactor or a cylindrical reactor, or 2 or 3 groups of these reactors connected in series.

For the production method of the present invention, it is preferable to increase the dissolution rate of a mixed gas formed of carbon monoxide and hydrogen in a linear unsaturated aldehyde having a rhodium catalyst dissolved therein, from the viewpoints of improving the effects of the present invention, that is, improving both of the catalytic activity and the dialdehyde selectivity. In a case of using the complete mixing bath type reactor or the cylindrical reactor, from the viewpoint of increasing the dissolution rate of the mixed gas, a mixed gas may be continuously supplied from the lower part of a reactor, or a loop-Venturi reactor as a cylindrical reactor equipped with an ejector having a mixing chamber.

Examples of the linear unsaturated aldehyde include 5-hexen-1-al, 6-hepten-1-al, 7-octen-1-al, 8-nonen-1-al, 9-decen-1-al, 10-undecen-1-al, and 11-dodecen-1-al. Among these, in a case of using 7-octen-1-al, the effects of the invention become significant.

Furthermore, in the production method of the present invention, 7-octen-1-al having a purity of 95% by mass or more can also be used. 7-Octen-1-al can be produced by, for example, isomerizing 2,7-octadien-1-ol in the presence of a copper-based catalyst. Examples of 7-octen-1-al thus produced include 1-octanal, 7-octen-1-ol, trans-6-octen-1-al, and cis-6-octen-1-al as by-products. With regard to these by-products, it is possible to subject 7-octen-1-al including such by-products to a hydroformylation reaction from the viewpoint of not significantly poisoning the rhodium catalyst for use in the production method of the present invention. That is, the scope of the invention is not limited according to the purity of the linear unsaturated aldehyde.

In the production method of the present invention, even when the reaction is carried out in the state in which the content of water in the reaction solution at a time of initiation of the reaction is 0.1 mmol/kg to 500 mmol/kg, and the content of a carboxylic acid in the reaction solution is 0.1 mmol/kg to 50 mmol/kg in terms of carboxyl groups, the reaction proceeds well. It is preferable that the content of water in the reaction solution at a time of initiation of the reaction is 0.1 mmol/kg to 50 mmol/kg. Further, it is preferable that the content of a carboxylic acid in the reaction solution is 0.1 mmol/kg to 25 mmol/kg in terms of carboxyl groups. Within a range satisfying the related conditions, the linear unsaturated aldehyde used as a raw material in the production method of the present invention may contain water and/or a carboxylic acid.

The production method of the present invention may be carried out in the presence of a solvent. Preferred examples of the solvent include the same ones as the solvents as described above which can be used for the preparation of a solution of the rhodium catalyst. In a case where the solvent is present, the use amount thereof is preferably 0.1% by mass to 20% by mass, and more preferably 1% by mass to 10% by mass with respect to the total reaction solution. Further, the amount of the solvent used means a total sum of the solvent supplied as a solution of the rhodium catalyst and a solvent separately supplied to the reaction system.

In the production method of the present invention, the amount of the rhodium in the reaction solution is preferably $1.0 \times 10^{-4}$ mmol/kg to $6.0 \times 10^{-1}$ mmol/kg, more preferably $1.0 \times 10^{-3}$ mmol/kg to $2.5 \times 10^{-1}$ mmol/kg, and still more preferably $1.0 \times 10^{-3}$ mmol/kg to $2.5 \times 10^{-2}$ mmol/kg, in terms of rhodium atoms. The amount of the bisphosphite (I) used in the reaction solution is preferably 1 molar times to 100 molar times, and more preferably 2 molar times to 20 molar times, with respect to rhodium atoms. Within such a range, a high catalytic activity and a high dialdehyde selectivity can be achieved.

In the production method of the present invention, the reaction temperature is preferably 50° C. to 130° C., and more preferably 100° C. to 120° C. If the reaction temperature is within the above range, a high catalytic activity and a high dialdehyde selectivity can be achieved, while not decomposing the rhodium catalyst.

In the production method of the present invention, the compositional ratio, carbon monoxide/hydrogen, of the mixed gas formed of carbon monoxide to hydrogen for use in the reaction, in terms of molar ratio, is usually in the range of 0.1/1 to 10/1, preferably in the range of 0.5/1 to 5/1, and more preferably in the range of 1/1 to 3/1. The pressure at a time of the reaction of the related mixed gas is preferably 0.5 MPa to 10.0 MPa (gauge pressure), and more preferably 1.0 MPa to 5.0 MPa (gauge pressure).

The characteristics of the production method of the present invention are that a hydroformylation reaction of the linear unsaturated aldehyde is carried out by setting the pressure of the mixed gas formed of carbon monoxide and hydrogen at a time of initiation of the reaction pressure to a relatively high value, and as the reaction proceeds, the reaction pressure of the mixed gas formed of carbon monoxide and hydrogen is reduced. More suitably, in the production method of the present invention, the reaction is carried out while controlling the reaction pressure of the mixed gas formed of carbon monoxide and hydrogen stepwise or continuously to a pressure corresponding to 30% to 80%, and preferably 40% to 70% of the pressure at a time of initiation of the reaction, in a step in which the conversion of the linear unsaturated aldehyde is more than 70%.

In an embodiment of the production method of the present invention, for example, in a case of using a reactor in a batch or semi-batch mode, the reaction is further carried out while controlling the reaction pressure of the mixed gas formed of carbon monoxide and hydrogen stepwise or continuously to a pressure accounting for 30% to 80%, and preferably 40% to 70% of the pressure at a time of initiation of the reaction, in a step in which the conversion of the linear unsaturated aldehyde is more than 70%. Alternatively, a plurality of reactors in a batch mode are connected to carry out a reaction in a first reactor until the conversion of the linear unsaturated aldehyde is more than 70%, and then the reaction solution in the first reactor is transferred to a second reactor in which the reaction pressure of the mixed gas formed of carbon monoxide and hydrogen accounts for 30% to 80% of one of the first reactor. Subsequently, the reaction may be carried out in a flow and continuous reaction mode, in which the reaction is continuously carried out. By controlling the reaction pressure in such a manner as the reaction proceeds, there is no reduction in the yield of the obtained dialdehydes and the amount of rhodium used can be cut down. As a result, the catalyst cost occupying the production cost of a dialdehyde can be cut down.

Moreover, in the production method of the present invention, a phosphorous compound other than the bisphosphite (I) may further coexist, if necessary. Examples of the phosphorous compound include phosphines such as triisopropylphosphine, tri-n-butylphosphine, tri-t-butylphosphine, tribenzylphosphine, triphenylphosphine, tris(p-methoxyphenyl)phosphine, tris(p-N,N-dimethylaminophenyl)phosphine, tris(p-fluorophenyl)phosphine, tri-o-tolylphosphine, tri-m-tolylphosphine, tri-p-tolylphosphine, tris(pentafluorophenyl)phosphine, bis(pentafluorophenyl)phenylphosphine, diphenyl(pentafluorophenyl)phosphine, methyldiphenylphosphine, ethyldiphenylphosphine, cyclohexyldiphenylphosphine, dimethylphenylphosphine, diethylphenylphosphine, 2-furyldiphenylphosphine, 2-pyridyldiphenylphosphine, 4-pyridyldiphenylphosphine, m-diphenylphosphinobenzenesulfonic acid or a metal salt thereof, p-diphenylphosphinobenzoic acid or a metal salt thereof, and p-diphenylphosphinophenylphosphonic acid or a metal salt thereof; and phosphites such as triethylphosphite, triphenylphosphite, tris(p-methoxyphenyl)phosphite, tris(o-methylphenyl)phosphite, tris(m-methylphenyl)phosphite, tris(p-methylphenyl)phosphite, tris(o-ethylphenyl)phosphite, tris(m-ethylphenyl)phosphite, tris(p-ethylphenyl)phosphite, tris(o-propylphenyl)phosphite, tris(m-propylphenyl)phosphite, tris(p-propylphenyl)phosphite, tris(o-isopropylphenyl)phosphite, tris(m-isopropylphenyl)phosphite, tris(p-isopropylphenyl)phosphite, tris(o-t-butylphenyl)phosphite, tris(p-t-butylphenyl)phosphite, tris(p-trifluoromethylphenyl)phosphite, tris(2,4-dimethylphenyl)phosphite, tris(2,4-di-t-butylphenyl)phosphite, and tris(2-t-butyl-4-methylphenyl)phosphite. In a case where the phosphorous compound further coexists, the use amount thereof is preferably 1 molar times to 100 molar times, and more preferably 2 molar times to 20 molar times, with respect to the rhodium atoms.

In the production method of the present invention, a nitrogen-containing compound may further coexist, if necessary. Examples of the related nitrogen-containing compound include triethylamine, tributylamine, tri-n-octylamine, N,N,N',N'-tetramethyl-1,2-diaminoethane, N,N,N',N'-tetramethyl-1,3-diaminopropane, N,N,N',N'-tetramethyl-1,4-diaminobutane, N,N-diethylethanolamine, triethanolamine, N-methylpiperidine, N-methylpyrrolidine, N-methylmorpholine, pyridine, picoline, lutidine, collidine, and quinoline. In a case where the nitrogen-containing compound further exists, the use amount thereof is preferably 100 molar times to 3000 molar times, and more preferably 500 molar times to 2000 molar times, with respect to the rhodium atoms. If the nitrogen-containing compound further coexists, a dialdehyde which is a desired product can be inhibited from being a high-boiling material by further undergoing a reaction under the reaction conditions.

In the production method of the present invention, the content of rhodium included in the reaction solution after completion of the hydroformylation reaction is as low as industrially available. Therefore, an operation of recovering rhodium from the reaction solution is not carried out and the reaction solution can be directly used as it is in the next reaction such as a hydrogenation reaction and a reductive amination reaction. Of course, a step of separating and purifying the dialdehyde from the reaction solution together with the rhodium catalyst component may be carried out, as desired. Such a method for separating and purifying the dialdehyde from the reaction solution is not particularly limited, and a known method may be applied. For example, low-boiling-point components can be evaporated from the hydroformylation reaction solution under reduced pressure and the residue can further be purified by distillation and separated from the distillation residue including unreacted raw materials, the dialdehyde, and the rhodium catalyst. The unreacted reaction raw materials and the distillation residue may be reused in the production method of the present invention. In addition, before the distillation and separation, the components constituting the rhodium catalyst may be separated by carrying out a method such as evaporation, extraction, and adsorption of residues.

EXAMPLES

Hereinbelow, the present invention will be described in more detail with reference to Examples and Comparative Examples, but is not limited to the related Examples and Comparative Examples in any case.

7-Octen-1-al used as a raw material in each of Examples and Reference Examples has a purity of 95.4% by mass, and the main impurities are 1-octanal, trans-6-octen-1-al, and cis-6-octen-1-al. Unless otherwise specified, preparation of the rhodium catalyst is carried out at room temperature and normal pressure in a nitrogen atmosphere, and as the raw material and the solvent, those which had been preliminarily purified by distillation and purged with nitrogen were used.

As a bisphosphite, compounds represented by the following chemical formulae were used:

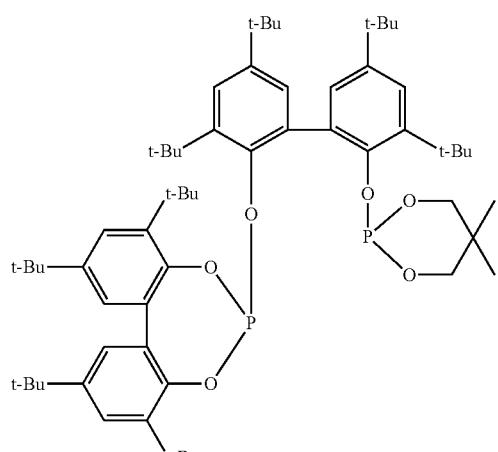

Bisphosphite A

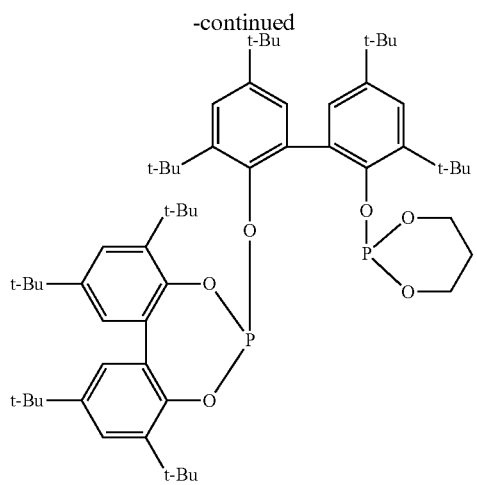

Bisphosphite B

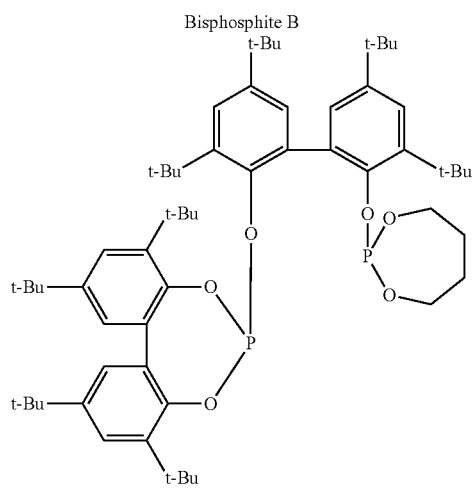

Bisphosphite C

These were synthesized by a known method.

The amount (conversion) of 7-octen-1-al used in the reaction solution and the amounts of 1,9-nonanedial, 2-methyl-1,8-octanedial, and other products, which are desired products, were analyzed and quantified by gas chromatography.

Example 1

To a 3-neck flask having an internal capacity of 100 mL, equipped with a magnetic rotor, were added 29.2 mg (0.113 mmol) of Rh(acac)(CO)$_2$, 744.7 mg (0.759 mmol) of bisphosphite A, and 77.38 g of toluene in a nitrogen atmosphere, and the mixture was stirred and dissolved at 50° C. for 30 minutes and then cooled to room temperature. The atmosphere was replaced with a mixed gas of carbon monoxide/hydrogen=1/1 (molar ratio) and then the mixture was further stirred for 30 minutes to prepare a solution of a rhodium catalyst.

On the other hand, the inside of an autoclave having an internal capacity of 3 L, equipped with a max blend blade, a rhodium catalyst solution inlet, a gas inlet, a gas outlet, and a sampling port, was replaced with a mixed gas atmosphere of carbon monoxide/hydrogen=1/1 (molar ratio), and then 717.00 g of 7-octen-1-al (purity of 95.4% by mass), 5.70 g (316.41 mmol) of water, and 2.20 g (15.26 mmol) of octanoic acid. The inside of the autoclave was pressurized to 2.0 MPa (gauge pressure) with a mixed gas of carbon monoxide/hydrogen=1/1 (molar ratio), and the temperature was raised to 110° C. while sufficiently stirring the mixture at 500 rpm. Then, 5.76 g (including 0.0084 mmol of rhodium atoms and 0.0559 mmol of bisphosphite A) of the rhodium catalyst solution previously prepared was pumped into the inside of the autoclave with a mixed gas of carbon monoxide/hydrogen=1/1 (molar ratio), and then the internal temperature was raised to 120° C. within 5 minutes while stirring. Further, the total pressure of the inside of the autoclave was set to 5.0 MPa (gauge pressure) using a mixed gas of carbon monoxide/hydrogen=1/1 (molar ratio) to initiate a reaction. The concentration of rhodium in the reaction solution at a time of initiation of the reaction was 0.0115 mmol/kg in terms of rhodium atoms, the amount of bisphosphite to be used was 6.72 molar times with respect to the rhodium atoms, the water content was 430 mmol/kg, and the carboxylic acid content was 20.88 mmol/kg in terms of carboxyl groups.

When the time at which the internal temperature of the reaction solution reached 120° C. was defined as 0, a time of initiation of the reaction, the conversion of 7-octen-1-al after 8 hours of the reaction was 85.2%, the selectivity for the dialdehydes was 92.2% (1,9-nonanedial/2-methyl-1,8-octanedial=84.6/15.4; hereinafter simply referred to as ratio of linear dialdehydes/branched dialdehydes), and the selectivity for isomers and the like (6-octen-1-al, octanal, and the like) was 7.8%. Thereafter, the pressure of the mixed gas of carbon monoxide/hydrogen=1/1 (molar ratio) in the inside of the autoclave was reduced to 2.0 MPa (gauge pressure) within 30 seconds, and the reaction was carried out for an additional 4 hours (a total reaction time of 12 hours). The conversion of 7-octen-1-al at a time of completion of the reaction was 97.3%, the selectivity for the dialdehydes was 91.9% (the ratio of linear dialdehydes/branched dialdehydes=85.0/15.0) (yield of the dialdehydes: 89.4%), and the selectivity for isomers and the like was 8.1%.

Example 2

The same reaction as in Example 1 except that water and octanoic acid were not added in Example 1 was carried out. The concentration of rhodium in the reaction solution at a time of initiation of the reaction was 0.0116 mmol/kg in terms of rhodium atoms, and the amount of bisphosphite to be used was 6.72 molar times with respect to the rhodium atoms.

The conversion of 7-octen-1-al after 8 hours of the reaction was 85.2%, the selectivity for the dialdehydes was 92.2% (the ratio of linear dialdehydes/branched dialdehydes=84.6/15.4), and the selectivity for isomers and the like was 7.8%. Thereafter, the pressure of the mixed gas of carbon monoxide/hydrogen=1/1 (molar ratio) in the inside of the autoclave was reduced to 2.0 MPa (gauge pressure) within 30 seconds, and the reaction was carried out for an additional 4 hours (a total reaction time of 12 hours). The conversion of 7-octen-1-al at a time of completion of the reaction was 97.3%, the selectivity for the dialdehydes was 91.9% (the ratio of linear dialdehydes/branched dialdehydes=85.0/15.0) (yield of the dialdehydes: 89.4%), and the selectivity for isomers and the like was 8.1%.

Example 3

The same reaction as in Example 1 except that 15.8 mg (0.061 mmol) of Rh(acac)(CO)$_2$ was used instead of 29.2 mg (0.113 mmol) of Rh(acac)(CO)$_2$, 401.7 mg (0.409 mmol) of bisphosphite A was used instead of 744.7 mg (0.759 mmol) of bisphosphite A, water and octanoic acid were not added, the pressure of the mixed gas of carbon monoxide/hydrogen=1/1 (molar ratio) in the inside of the autoclave was set to 5.0 MPa (gauge pressure) until 12 hours from the initiation of the reaction, then the pressure of the mixed gas of carbon monoxide/hydrogen=1/1 (molar ratio) in the inside of the autoclave was reduced to 2.0 MPa (gauge pressure) within 30 seconds, and the reaction was carried out for an additional 6 hours (a total reaction time of 18 hours) in Example 1 was carried out. The concentration of rhodium in the reaction solution at a time of initiation of the reaction was 0.0063 mmol/kg in terms of rhodium atoms, and the amount of bisphosphite to be used was 6.7 molar times with respect to the rhodium atoms.

The conversion of 7-octen-1-al after 12 hours of the reaction was 84.7%, the selectivity for the dialdehydes was 89.4% (the ratio of linear dialdehydes/branched dialdehydes=84.6/15.4), and the selectivity for isomers and the like was 10.6%. Thereafter, the pressure of the mixed gas of carbon monoxide/hydrogen=1/1 (molar ratio) in the inside of the autoclave was reduced to 2.0 MPa (gauge pressure). The conversion of 7-octen-1-al after an additional 6 hours of the reaction was 96.7%, the selectivity for the dialdehydes was 89.2% (the ratio of linear dialdehydes/branched dialdehydes=84.9/15.1) (yield of the dialdehydes: 86.3%), and the selectivity for isomers and the like was 10.2%.

Example 4

The same reaction as in Example 1 except that 33.6 mg (0.130 mmol) of Rh(acac)(CO)$_2$ was used instead of 29.2 mg (0.113 mmol) of Rh(acac)(CO)$_2$, 856.4 mg (0.873 mmol) of bisphosphite B was used instead of 744.7 mg (0.759 mmol) of bisphosphite A, water and octanoic acid were not added, the pressure of the mixed gas of carbon monoxide/hydrogen=1/1 (molar ratio) in the inside of the autoclave was set to 5.0 MPa (gauge pressure) until 8 hours from the initiation of the reaction, then the pressure of the mixed gas of carbon monoxide/hydrogen=1/1 (molar ratio) in the inside of the autoclave was reduced to 2.0 MPa (gauge pressure) within 30 seconds, and the reaction was carried out for an additional 4 hours (a total reaction time of 12 hours) in Example 1 was carried out. The concentration of rhodium in the reaction solution at a time of initiation of the reaction was 0.0134 mmol/kg in terms of rhodium atoms, and the amount of bisphosphite to be used was 6.7 molar times with respect to the rhodium atoms.

The conversion of 7-octen-1-al after 8 hours of the reaction was 83.8%, the selectivity for the dialdehydes was 92.2% (the ratio of linear dialdehydes/branched dialdehydes=79.6/20.4), and the selectivity for isomers and the like was 7.8%. Thereafter, the pressure of the mixed gas of carbon monoxide/hydrogen=1/1 (molar ratio) in the inside of the autoclave was reduced to 2.0 MPa (gauge pressure). The conversion of 7-octen-1-al after an additional 4 hours of the reaction was 96.8%, the selectivity for the dialdehydes was 92.0% (the ratio of linear dialdehydes/branched dialdehydes=80.1/19.9) (yield of the dialdehydes: 89.1%), and the selectivity for isomers and the like was 8.0%.

Example 5

The same reaction as in Example 1 except that 47.3 mg (0.183 mmol) of Rh(acac)(CO)$_2$ was used instead of 29.2 mg (0.113 mmol) of Rh(acac)(CO)$_2$, 1206.4 mg (1.229 mmol)

of bisphosphite C was used instead of 744.7 mg (0.759 mmol) of bisphosphite A, water and octanoic acid were not added, the pressure of the mixed gas of carbon monoxide/hydrogen=1/1 (molar ratio) in the inside of the autoclave was set to 5.0 MPa (gauge pressure) until 8 hours from the initiation of the reaction, then the pressure of the mixed gas of carbon monoxide/hydrogen=1/1 (molar ratio) in the inside of the autoclave was reduced to 2.0 MPa (gauge pressure) within 30 seconds, and the reaction was carried out for an additional 4 hours (a total reaction time of 12 hours) in Example 1 was carried out. The concentration of rhodium in the reaction solution at a time of initiation of the reaction was 0.0189 mmol/kg in terms of rhodium atoms, and the amount of bisphosphite to be used was 6.72 molar times with respect to the rhodium atoms.

The conversion of 7-octen-1-al after 8 hours of the reaction was 83.4%, the selectivity for the dialdehydes was 92.7% (the ratio of linear dialdehydes/branched dialdehydes=79.6/20.4), and the selectivity for isomers and the like was 7.8%. Thereafter, the pressure of the mixed gas of carbon monoxide/hydrogen=1/1 (molar ratio) in the inside of the autoclave was reduced to 2.0 MPa (gauge pressure). The conversion of 7-octen-1-al after an additional 4 hours of the reaction was 96.9%, the selectivity for the dialdehydes was 92.4% (the ratio of linear dialdehydes/branched dialdehydes=80.0/20.0) (yield of the dialdehydes 89.5%), and the selectivity for isomers and the like was 7.6%.

Reference Example 1

Comparison with Examples 1 and 2

The same reaction as in Example 1 except that 33.4 mg (0.130 mmol) of Rh(acac)(CO)$_2$ was used instead of 29.2 mg (0.113 mmol) of Rh(acac)(CO)$_2$, 851.7 mg (0.868 mmol) of bisphosphite A was used instead of 744.7 mg (0.759 mmol) of bisphosphite A, water and octanoic acid were not added, and the reaction was carried out for 12 hours at a pressure of the mixed gas of carbon monoxide/hydrogen=1/1 (molar ratio) in the inside of the autoclave constantly set to 5.0 MPa (gauge pressure) in Example 1 was carried out. The concentration of rhodium in the reaction solution at a time of initiation of the reaction was 0.0134 mmol/kg in terms of rhodium atoms, and the amount of bisphosphite to be used was 6.67 molar times with respect to the rhodium atoms.

The conversion of 7-octen-1-al after the reaction was 96.7%, the selectivity for the dialdehydes was 92.5% (the ratio of linear dialdehydes/branched dialdehydes=84.6/15.4) (yield of the dialdehydes: 89.4%), and the selectivity for isomers and the like was 7.5%.

Reference Example 2

Comparison with Example 3

The same reaction as in Example 1 except that 17.7 mg (0.069 mmol) of Rh(acac)(CO)$_2$ was used instead of 29.2 mg (0.113 mmol) of Rh(acac)(CO)$_2$, 451.0 mg (0.460 mmol) of bisphosphite A was used instead of 744.7 mg (0.759 mmol) of bisphosphite A, water and octanoic acid were not added, and the reaction was carried out for 18 hours at a pressure of the mixed gas of carbon monoxide/hydrogen=1/1 (molar ratio) in the inside of the autoclave constantly set to 5.0 MPa (gauge pressure) in Example 1 was carried out. The concentration of rhodium in the reaction solution at a time of initiation of the reaction was 0.0071 mmol/kg in terms of rhodium atoms, and the amount of bisphosphite to be used was 6.67 molar times with respect to the rhodium atoms.

The conversion of 7-octen-1-al after the reaction was 95.3%, the selectivity for the dialdehydes was 90.5% (the ratio of linear dialdehydes/branched dialdehydes=84.6/15.4) (yield of the dialdehydes: 86.2%), and the selectivity for isomers and the like was 9.5%.

In Example 1, the content of water in the reaction solution at a time of initiation of the reaction was 430 mmol/kg, and the carboxylic acid content was 20.88 mmol/kg in terms of carboxyl groups. That is, 7-octen-1-al was subjected to a hydroformylation reaction in the coexistence of 5600 molar times or more of water and 260 molar times or more of octanoic acid with respect to bisphosphite A. From the results of residue rate tests at 125° C. with the addition of 100 mg of bisphosphite in 100 ml of toluene with a water content of 70 ppm, as described in PTL 1, it is expected that bisphosphite has low stability and hardly functions as a catalyst, but surprisingly, the reaction proceeded well as described in Example 1. That is, even under the conditions that the content of water in the reaction solution at a time of initiation of the reaction is 0.1 mmol/kg to 500 mmol/kg, and the content of a carboxylic acid in the reaction solution is 0.1 mmol/kg to 50 mmol/kg in terms of carboxyl groups, the production method of the present invention can be carried out well.

In Example 2 and Reference Example 1, the amount of rhodium to be used (with a concentration conversion in terms of rhodium atoms in the reaction solution at a time of initiation of the reaction) when a dialdehyde is obtained in a yield of 89.4% after 12 hours of the reaction is 0.0116 mmol/kg in Example 2, but is 0.0134 mmol/kg in Reference Example 1. That is, in Example 2, in which the production method of the present invention that reduces the reaction pressure as the reaction proceeds is applied, the amount of rhodium used can be cut down by about 13%, as compared with Reference Example 1 in which the reaction pressure is kept at a constant pressure.

Similarly, in Example 3 and Reference Example 2, the amount of rhodium to be used (with a concentration conversion in terms of rhodium atoms in the reaction solution at a time of initiation of the reaction) when a dialdehyde is obtained in a yield of 86.3% after 18 hours of the reaction is 0.0063 mmol/kg in Example 3, but is 0.0071 mmol/kg in Reference Example 2. That is, in Example 3, in which the production method of the present invention is applied, the amount of rhodium used can be cut down by about 11%, as compared with Reference Example 2 in which the reaction pressure is kept at a constant pressure.

From these Examples, it can be considered that according to the production method of the present invention that reduces the reaction pressure as the reaction proceeds, and suitably, in a step in which the conversion of the linear olefinic compound having each of an ethylenic double bond and an aldehyde group on each end of the molecule is more than 70%, the amount of rhodium used can be cut down, thus contributing to cutting down of the production cost of the dialdehyde, by controlling the pressure stepwise or continuously to 30% to 80% of the pressure at a time of initiation of the reaction.

From Examples 4 and 5, it can be considered that the production method of the present invention can also be effectively carried out in bisphosphites B and C.

INDUSTRIAL APPLICABILITY

By the method of the present invention, it is possible to industrially advantageously produce a dialdehyde having a production ratio of linear dialdehydes to branched dialdehydes of 80/20 to 90/10. The method of the present invention is useful as, for example, a method for producing a dialdehyde mixture (NL/MOL=80/20 to 90/10) with 1,9-nonanedial/2-methyl-1,8-octanedial (NL/MOL), which becomes a synthesis intermediate of a diol mixture of 1,9-nonanediol and 2-methyl-1,8-octanediol (a content of 1,9-nonanediol of 80% by mass to 90% by mass), from 7-octen-1-al. A diol mixture of 1,9-nonanediol and 2-methyl-1,8-octanediol can be obtained from the dialdehyde mixtures, and such diol mixtures are useful as a raw material for producing polycarbonates, polyesters, polyurethanes, or the like, a raw material for paints (polyester paints or epoxy resin paint), a resin modifier for polyester resins or epoxy resins, or the like.

The invention claimed is:

1. A method for producing a dialdehyde, comprising reacting a linear olefinic compound having each of an ethylenic double bond and an aldehyde group on each end of the molecule with carbon monoxide and hydrogen in the presence of a rhodium catalyst comprising a bisphosphite of (I) and a rhodium compound, wherein the reaction pressure of a mixed gas formed of carbon monoxide and hydrogen is decreased as the reaction proceeds, and wherein the reaction solution at a time of initiation of the reaction comprises from 0.1 mmol/kg to 500 mmol/kg of water, and from 0.1 mmol/kg to 50 mmol/kg of a carboxylic acid in terms of carboxyl group:

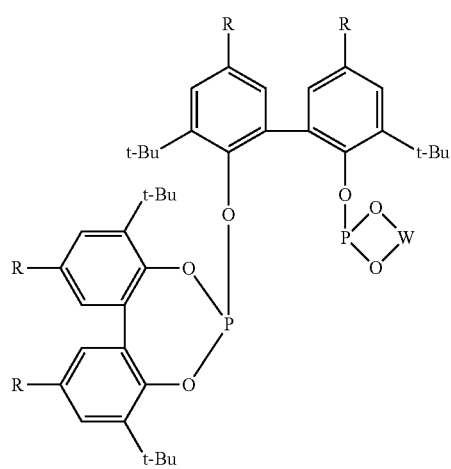

wherein R is a hydrogen atom, an alkyl group having 1 to 4 carbon atoms, or an alkoxy group having 1 to 4 carbon atoms, and W is an alkylene group having 1 to 20 carbon atoms, a cycloalkylene group having 5 to 18 carbon atoms, or an alkylene-arylene group having 7 to 11 carbon atoms.

2. The method of claim 1, wherein the reaction pressure of a mixed gas formed of carbon monoxide and hydrogen is controlled stepwise or continuously to 30% to 80% of the pressure at a time of initiation of the reaction in which the conversion of the linear olefinic compound having each of an ethylenic double bond and an aldehyde group on each end of the molecule is more than 70%.

3. The method of claim 2, wherein a plurality of reactors are connected, the reaction is carried out in a first reactor until the conversion of the linear olefinic compound having each of an ethylenic double bond and an aldehyde group on each end of the molecule is more than 70%, and then the reaction solution in the first reactor is transferred to a second reactor in which the reaction pressure of the mixed gas formed of carbon monoxide and hydrogen is 30% to 80% of one of the first reactor to successively carry out the reaction.

4. The method of claim 1, wherein the linear olefinic compound having each of an ethylenic double bond and an aldehyde group on each end of the molecule is selected from the group consisting of 5-hexen-1-al, 6-hepten-1-al, 7-octen-1-al, 8-nonen-1-al, 9-decen-1-al, 10-undecen-1-al, and 11-dodecen-1-al.

5. The method of claim 1, wherein R is an alkyl group having 1 to 4 carbon atoms or an alkoxy group having 1 to 4 carbon atoms, and W is an alkylene group having 1 to 20 carbon atoms.

6. The method of claim 5, wherein R is a t-butyl group and W is an alkylene group having 2 to 5 carbon atoms.

7. The method of claim 1, wherein
an amount of the rhodium in the reaction solution is from $1.0 \times 10^{-4}$ mmol/kg to $6.0 \times 10^{-1}$ mmol/kg in terms of rhodium atoms,
an amount of bisphosphite is from 1 molar times to 100 molar times with respect to the rhodium atoms,
a reaction temperature is from 50° C. to 130° C.,
a compositional ratio of carbon monoxide to hydrogen, carbon monoxide/hydrogen, is from 0.1/1 to 10/1 in terms of molar ratio, and
a pressure at a time of initiation of the reaction is from 0.5 MPa to 10 MPa (gauge pressure).

* * * * *